(12) United States Patent
Lin et al.

(10) Patent No.: US 7,197,196 B2
(45) Date of Patent: Mar. 27, 2007

(54) MINIATURE SURFACE PLASMON RESONANCE WAVEGUIDE DEVICE WITH SINUSOIDAL CURVATURE COMPENSATION

(75) Inventors: Chii-Wann Lin, Taipei (TW); Cheng-Lung Lee, Yongkang (TW); Way-Seen Wang, Taipei (TW); Chih Kung Lee, Taipei (TW)

(73) Assignee: National Taiwan University, Taipei (TW)

( * ) Notice: Subject to any disclaimer, the term of this patent is extended or adjusted under 35 U.S.C. 154(b) by 353 days.

(21) Appl. No.: 10/994,777

(22) Filed: Nov. 22, 2004

(65) Prior Publication Data

US 2006/0109471 A1    May 25, 2006

(51) Int. Cl.
*G02B 6/26* (2006.01)
*G01N 21/55* (2006.01)

(52) U.S. Cl. .................. 385/12; 385/129; 356/445
(58) Field of Classification Search ............. 385/12; 356/445
See application file for complete search history.

(56) References Cited

U.S. PATENT DOCUMENTS

| | | | |
|---|---|---|---|
| 5,647,030 A * | 7/1997 | Jorgenson et al. ............ 385/12 |
| 5,835,645 A * | 11/1998 | Jorgenson et al. ............ 385/12 |
| 6,873,417 B2 * | 3/2005 | Bahatt et al. ............... 356/445 |
| 2003/0210399 A1 * | 11/2003 | Bahatt et al. ............... 356/445 |
| 2006/0146332 A1 * | 7/2006 | Lin et al. .................... 356/445 |
| 2006/0215165 A1 * | 9/2006 | Melman ..................... 356/445 |
| 2006/0262313 A1 * | 11/2006 | Bahatt et al. ............... 356/445 |
| 2006/0289761 A1 * | 12/2006 | Nabet et al. ............. 250/336.1 |

* cited by examiner

*Primary Examiner*—Frank G. Font
*Assistant Examiner*—James P. Hughes
(74) *Attorney, Agent, or Firm*—Schmeiser, Olsen & Watts

(57) ABSTRACT

The present invention is in related to a miniature surface plasmon resonance waveguide device with sinusoidal curvature compensation and at least comprises: a substrate, a waveguide structure, a sensing film layer and a cover layer, wherein the waveguide structure is configured with the function of sinusoidal curvature compensation and installed above the substrate, further that, the waveguide structure includes a light input port and a light output port; the sensing film layer is on a special region of the waveguide structure, the special region is a sensing region; the cover layer is upper than the substrate and has an opening. By means of the optimal curve figure of the sinusoidal curvature compensation, attenuation of light energy can be minimized while in propagation, and allows the input and output of the light on the same side of the device.

15 Claims, 7 Drawing Sheets

MINIATURE SURFACE PLASMON RESONANCE WAVEGUIDE DEVICE WITH SINUSOIDAL CURVATURE COMPENSATION

FIELD OF THE INVENTION

The present invention generally relates to a optical waveguide type surface plasmon resonance (SPR) sensing device and more particularly relates to a miniature waveguide surface plasmon resonance sensing device with sinusoidal curvature compensation, which is applicable in the biomedical sensing for bio-molecules.

BACKGROUND OF THE INVENTION

A considerable attention from academies, governments and private institutions in many countries is being given to the development of biochips. In the field of deoxyribonucleic acid (DNA) chips, such as DNA sequences analyses, capillary electrophoreses, nucleic acid amplification, and parallel gene expression analyses are progressing toward maturity. Based on these developments, a series of emerging analytical methods are becoming available quickly, for instance, cell separation, cell-mediated immuno-assay, and high-throughput assays for new drug screening, which combined with combinatorial chemistry. The biochips are being fabricated by low cost plastic technology and elastomers, in addition to presently dominating silicon technology.

A unique trait of a biosensor is its combination with biological elements to form part of sensing mechanism, and by connecting with transducers to achieve the purpose of the detection of biological reactions; moreover, its integration with Micro-Electro-Mechanical Systems (MEMS) processes is named "bio-chip". Among the related technologies of chip development, optical methods for detection offer high sensitivity and possible high throughput solutions, wherein fluorescence has been the chosen methods for many applications in the past. Surface plasmon resonance (SPR) becomes an emerging research tool for its non-labeling and real-time detection traits. The SPR biosensor exploits the optical principle of SPR as the transducer for biomolecule recognition. As the changes of composition, concentration or constituent within the sensing volume, it might result in a change of refractive index, and in turn a change in the resonant angle of SPR through the dissipated light energy. SPR, existing at the interface between a metal and a dielectric, is excited by a TM-polarized light beam, where the electrical field and magnetic field vectors are perpendicular and parallel to the plane of the interface respectively and are decaying exponentially on both directions. After the surface modification of the sensing area, protein molecules, e.g. antigens or antibodies, can be immobilized onto the activated surface for subsequently hybridized with corresponding molecules through recognition processes. Theoretically, only the bonded analytes, after washing, could influence the intensity of the reflected light. The substances, which are not within the sensing volume of surface plasmon wave, wouldn't affect the detecting outcome. Therefore, this method can offer very high discrimination of few hundred nanometers.

From the literature reviews, the state of art technology for SPR waveguide sensors is mainly on planar waveguide SPR sensors. The fabrication processes of such a waveguide sensor starts with a BK7 glass substrate, followed by thin film processes and etching to form a metallic pattern in a waveguide, and finally ion implantation into the substrate by high temperature ion exchange to change refractive index of the substrate. A layer of metallic film and a buffer layer of dielectric material are used for adjusting the sensing range, which are required for the waveguide to realize the SPR phenomenon. Another method is for optical-fiber type SPR sensors, which are made by stripping the cladding of the optical fiber and followed by a metal plating process.

There are two major categories of SPR waveguide detection schemes; one is by intensity modulation while the other is by wavelength modulation. The intensity type is the popular one and the earliest one, which satisfies the demands of higher intensity of single-wavelength laser beam to balance the loss of waveguides. The wavelength type is the latest one beneficial by the progress of the latest techniques in optical fiber, and its detection wouldn't need intense light for a moderate loss. An advantage of the wavelength type over the intensity type in detection is the wider dynamic range of the refractive index, and eliminates the constraint of narrow frequency bandwidth of the laser beam. In the curvature waveguide, it is known to have energy loss at the curvature location, so that the curvature radius has to be larger than the minimum curvature radius, which is subject to the refractive index difference of fiber core and sensing volume. It is actually depending on the experimental conditions.

The SPR sensing devices of the related arts use a glass slide as the substrate, where the majority is planar configuration, which is not handy for the detection by the portable instrument. The waveguide design is also by a straight-in-straight-out fashion, lacks of an optimum in size and also fails to offer a handy user interface.

SUMMARY OF THE INVENTION

As a consequence, the objective of the present invention provides a miniature SPR waveguide device with sinusoidal curvature compensation, trying to seek compensation for energy loss of light by an optimal design of sinusoidal curvature, aligning the input and the output on the same side, and accompanying a plated metallic film in a characteristic wavelength that the SPR phenomenon can occur.

The present invention provides a miniature SPR waveguide device with sinusoidal curvature compensation comprising at least: a substrate; an waveguide structure; a sensing film layer and a cover layer, where the waveguide structure features sinusoidal curvature compensation, rests on top of the substrate and has an input port and an output port for light coupling; the sensing film layer stands at a specific area on a top of the waveguide structure, the specific area is a sensing area; and the cover layer covers the whole device and has an open hole around the sensing area.

The present invention further comprises a light source and a spectrophotometer, which the light source provides the input light signal of the input port; the spectrophotometer receives the output light signal from the output port. Through the waveguide structure with sinusoidal curvature compensation, light is being guided from the input port of the waveguide, propagating along the path having sinusoidal curvature compensation, crossing the sensing area and emitting from the output port of the waveguide structure.

The waveguide structure of the present invention has dual sinusoidal curvatures for compensation which combine to form a Y-shaped structure, couples with a lens device standing at one end of the Y-shaped structure and featuring converging light into the input port of the waveguide structure, where light propagates along the path having sinusoidal curvature compensation, crosses the sensing area and emits from the output port of the waveguide structure by means of the lens device.

Another waveguide structure of the present invention has triple sinusoidal curvatures for compensation. As light is being guided into the input portion of the waveguide structure, it propagates along the path having sinusoidal curvature compensation, crosses the sensing area and emits from the output portion of the waveguide structure.

Other objectives, characteristics and advantages in addition to the above description of the present invention will become apparent from the following preferred embodiment in conjunction with the illustrative drawings.

DETAILED DESCRIPTION OF THE INVENTION

[Principles of Surface Plasmon Measurement]

I. Surface Plasmon Theory

Figure 1:
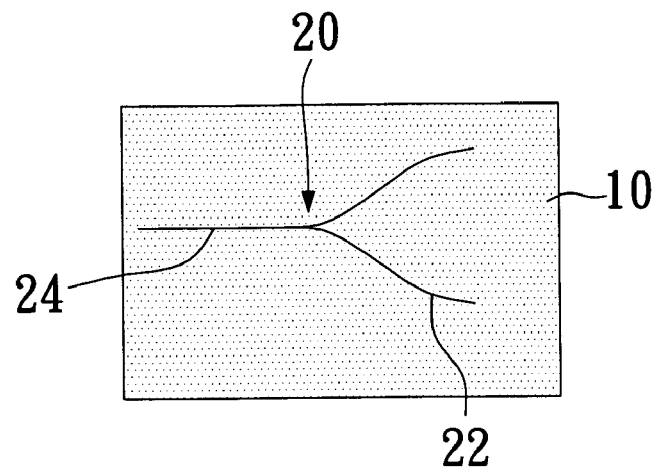
FIG. 1 is a schematic view of a miniature SPR waveguide device with dual sinusoidal curvatures for compensation of the present invention.

SPR can be derived from the free electron theory of metal conductor. With proper momentum matches of coupling electromagnetic wave, group of excited electrons ($10^{28}$ pc/m$^3$) behave like a forced oscillator and induced wave propagation along the interface of the metal and dielectric medium, which is known as surface plasmon wave (SPW, same as SEW). The phenomenon of anomalous diffraction on diffraction gratings due to the excitation of surface plasmon waves was first described in the beginning of the twentieth century by R. W. Wood.

The surface plasmon wave can be excited by p-polarized light which has its electric field polarized parallel to an incident plane, i.e. a TM-polarized wave. Once an incident angle of the p-polarized light being greater than a critical angle, a total internal reflection (TIR) happens, which gives rise to an evanescent field perpendicular to the surface and heading away from an incident surface so that the energy is not totally reflected. The evanescent field is capable of activating some dipoles, and such dipoles may be resonated by the electric field of the incident light and propagated on the inner surface by way of surface charge density oscillation while the incident angle equal to the resonance angle, therefore the electric field intensity shall be the most on the interface. That is the phenomena of SPR, and the reflected intensity shall be a drop suddenly, called attenuation total reflection (ATR).

SEW, similar to an evanescent wave, has its maximum value of electric field at the interface and decays exponentially with a distance away from the metallic surface. The electric field of SPR attenuates in an asymmetry fashion and decays faster in a metallic layer while slower in a dielectric medium. It thus contributes to its great sensitivity to the minute changes of dielectric medium in the vicinity of interface. Besides, surface plasmon waves may decay in radiation (subject to the thickness and roughness of the metallic surface) and may transform into heat absorbed by materials (related to the imaginary part of a dielectric constant).

II. Conditions for SPR Coupling

With Maxwell's equations for the wave equations and the boundary conditions for SPR excitation, the relationship that the transverse wave vector $k_x$ of the incident light is able to couple with the wave vector $k_{sp}$ of SPR, the incident angle and the dielectric constant among interfaces may satisfy the following conditions:

Coupling condition:

$$k_x = k_{sp},$$

where $$k_x = \frac{\omega}{c}\sqrt{\varepsilon_p}\sin\theta,$$

$$k_{sp} = \frac{\omega}{c}\sqrt{\frac{\varepsilon_m(\omega)\varepsilon_s(\omega)}{\varepsilon_m(\omega)+\varepsilon_s(\omega)}},$$

(c is light speed; $\omega$, the angular frequency of light; $\epsilon_p'\epsilon_m'\epsilon_s$, the dielectric constants for the prism, the metal and the sensing interface respectively; and $\theta$, the incident angle of light.)

At $k_x=k_{sp}$, SPW is excited. Once the $k_x$ is known by manipulating the incident wavelength or angle, the variation of dielectric constant for tested object is obtained.

The coupling condition mentioned above, light propagated internally which incident angle may not be obtained; however, $k_x$ can be known by figuring waveguide dispersion equations.

The phenomenon is not generated by that light emitting onto a metal surface and must be excited by a light-coupler to enhance the wave vector along the interface. However, there are three general configurations of SPR devices altering the momentum of photons in a way that fulfills the resonance criterion: prisms, gratings and waveguide-based SPR systems. The prism coupler-based SPR system is the most widely used configuration for easy preparation and assembly. The waveguide-based system gains additional attentions for possible integration with other optical components, which allows further miniaturization for minute samples and small footprint sensor system.

III. Characteristics of SPR and Equations EM theories of SEW:

(1) At the interface of metal/dielectric: $\bar{\epsilon}_1=\epsilon_1'+i\epsilon_1''$, $\bar{\epsilon}_2=\epsilon_2$.

(2) Interface characteristics: $\epsilon_1''<|\epsilon_1'|$, $\epsilon_1'<0$, $|\epsilon_1'|>\epsilon_2$.

(3) Intensity: longitudinal exponential decay as $\exp(-|k_{zi}||z|)$, lateral exponential decay as $\exp[-2\mathrm{Im}(k_x)x]$.

(4) Longitudinal depth of propagation: longitude as $z=1/|k_{zi}|$, that is in medium (dielectric constant $\epsilon_2$), $z_2=\lambda/2\pi*\sqrt{(\epsilon_1'+\epsilon_2)/\epsilon_2^2}$; in metal $z_1=\lambda/2\pi*\sqrt{(\epsilon_1'+\epsilon_2)/\epsilon_1'^2}$.

(5) Lateral length of propagation:

$$L_x = 1/|2\mathrm{Im}(k_x)| = \frac{c}{\omega}\left(\frac{\varepsilon_1'\varepsilon_2}{\varepsilon_1'+\varepsilon_2}\right)^{-3/2}\frac{\varepsilon_1'^2}{\varepsilon_1''}.$$

(6) A light-coupler is a must (grating coupler, prism coupler, or waveguide coupler).

[Theories of Waveguide Propagation]

There are two approaches in dealing with the theories of waveguides: one is from the geometrical optics, and the other is from the wave optics. If a incident light of wavelength $\lambda$ is much smaller than the lateral width of an waveguide, the wavelength $\lambda$ can be approximately taken as near zero; therefore, one can ignore the diffraction phenomenon in the wave attribute of light, and treat the light beam as a cone of light with zero divergence angle. Hence, this approach is also called a light-ray method. A light beam signifies information of direction and speed of the propagation, but tells no clues on phase and polarization. The major concerns include (1.) an incident angle of light makes a happening for total internal reflection in the waveguide, a light beam propagating inside the waveguide can then be assured, and the incident angle of the light beam may continually vary within a certain range. (2.) light waves to be investigated only that within the waveguide core, where electromagnetic fields outside the core is completely neglected, which is also compliant with the approximation of the wavelength $\lambda$ approaching zero. Strictly speaking, it would be better to describe that light propagating in the waveguide by way of the electromagnetic fields (i.e., the wave optics). Based on electromagnetic wave equations and boundary conditions in the waveguide, the form of electromagnetic fields inside the waveguide can be explored. This approach offers a precise solution but with a complicated solving procedure with various sorts of approximations so as to that the geometric optics being easier.

Light refraction analysis in a homogeneous waveguide: The homogeneous waveguide means the distribution of the refractive index in the core and in the cladding is uniform, which also means the refractive index is a radius-independent constant. A realization of total internal reflection in the waveguide requires the refractive index of the core, n1 larger than that of the cladding, n2, which is n1>n2.

There are two kinds of light rays, meridian ray and precession ray, propagating in the waveguide subject to the definition of incident plane:

a plane for propagating light wave is the meridian plane. The meridian plane intersects an axis of the light beam is called the meridian ray. Once the criterion of total internal reflection is satisfied, the light beam propagates in a zigzag pattern within the core, encounters a reflection each time impinging on the boundary of the core and the cladding, and intersects the axis as it is reflected. The precession ray indicates a light beam that its incidence and reflection are not intersecting with the axis, and it proceeds forward in a spiral fashion where the projected trajectory on a waveguide sectional plane forms a polygon (not really closed).

[Characteristic Parameters of Homogeneous Waveguide]

I. Refractive-Index Difference:

The refractive-index difference between core index n1 and cladding index n2 of a waveguide decides the value of a critical angle. The bigger the index difference, based on Snell's theory $\sin\theta=n2/n1$, the smaller the critical angle, and easier to deploy total internal reflection. The bigger the index difference the smaller the critical angle, which results in a large number of modes for light propagating in the waveguide and easily giving rise to the modal dispersion. Therefore, the Refractive-index difference $\Delta$ is as:

$$\Delta = \frac{n_1^2 - n_2^2}{2n_1} \approx \frac{n_1 - n_2}{n_1}, \text{ and}$$

$\Delta\approx 0.003$ for single mode, $\Delta\approx 0.01$ for multi-mode.

II. Numerical Aperture (NA):

Numerical aperture is an important parameter for the light-gathering ability of an waveguide while light propagating through waveguide from a surface thereof. That is, NA represents a value for the ability of capturing light by the waveguide. There are two kinds of light rays, meridian ray and precession ray, for light propagating in the waveguide. Normally, the meridian ray defines NA. An angle $\theta_a$ is defined by the incident light and the waveguide axis, and the light between the angle $\theta_a$ of the cone may satisfy total reflection in the waveguide to form a propagating mode. Other light outside the cone can propagate in the waveguide but not complying with the total reflection and only be reflected the waveguide cladding to form a radiation mode. A critical angle $\theta_c$ is defined as a sinusoidal value of the angle $\theta_a$, which means $\theta_c=\sin\theta_a$, called the numerical aperture of the waveguide.

$$NA=\sin\theta_a=n_1\sqrt{(2\Delta)},$$

where a value of 0.15~0.24 with an acceptable error of 0.02 is accepted.

III. Refractive Index Distribution in Waveguide:

The distribution of refractive index on a sectional plane of the waveguide represents another important parameter of light characteristics of the waveguide, which is called sectional index, $\alpha$. The numerical aperture and wave dispersion of the waveguide are related to the distribution of refractive index of the waveguide. In order to decrease the dispersion and raise the bandwidth of the waveguide, a thoughtful consideration for the distribution of refractive index in design is demanded. The sectional refractive index distribution of the waveguide is related to the radial coordinate $\gamma$. Using $n(\gamma)$ to represents the sectional refractive index distribution.

For a step-index waveguide, the sectional refractive index distribution equation is as follows:

$$n(r) = \begin{cases} n_1 & r \leq a \\ n_2 & r \geq a \end{cases}, \text{ and}$$

for a graded-index waveguide, the sectional refractive index distribution equation is:

$$n(r) = \begin{cases} n_1[1 - 2\Delta(\frac{r}{a})^\alpha]^{\frac{1}{2}} & r \leq a \\ n_2 & r \geq a \end{cases}$$

where $\alpha$ is cross-section index.

As $\alpha=\infty$, the distribution of refractive index in the waveguide is called a step-index type, and the waveguide is called a step-index waveguide. As $\alpha=2$, the distribution of refractive index in the waveguide is a parabola shape, and the waveguide is called a parabola waveguide or a square-law waveguide. In general, a multi-mode waveguide has the a value at around 2 which is called a graded-index waveguide or a tapered waveguide.

IV. Relations Between Waveguide Modes and Dispersion:

The most important parameter in a waveguide is the mode numbers, which decides the dispersion relationship as a light beam propagating in the waveguide. Different modes give rise to the different dispersion relationship and the different types of energy distribution where the dispersion relates to wavelength. For instance, a step-index waveguide has a distribution of refractive index as follows, $$\frac{n_3}{n_1},$$
$$n_2$$

which is a homogenous waveguide, the dispersion of fundamental mode according to the wave optics equations is as follows:

$$\tan rd = \frac{rd\left\{\left(\frac{n_1}{n_2}\right)^2[(n_1^2-n_2^2)(k_0d)^2-(rd)^2]^{\frac{1}{2}} + \left(\frac{n_1}{n_3}\right)^2[(n_1^2-n_3^2)(k_0d)^2-(rd)^2]^{\frac{1}{2}}\right\}}{(rd)^2 - \left(\frac{n_1}{n_2}\right)^2[(n_1^2-n_2^2)(k_0d)^2-(rd)^2]^{\frac{1}{2}}\left(\frac{n_1}{n_3}\right)^2[(n_1^2-n_3^2)(k_0d)^2-(rd)^2]^{\frac{1}{2}}}$$

where $k_0=\omega\sqrt{u_0\epsilon_0}$, and $r=\sqrt{k_0^2 n_1^2 - k_x^2}$, wherein $n_1$, $n_2$, $n_3$ are the refractive indices for the different layers, and d represents the thickness of the waveguide.

In the fundamental mode, the relationship between $k_x$ and $\omega$ can be known from the above dispersion equation.

[Curvature Loss of Waveguide]

As light travels in a curved structure of the waveguide, it is always accompanied with energy loss. From the ray optics, this energy loss comes from the small difference of refractive indices between a waveguide and its adjacent interface. The incident angle, where total internal reflection occurs for a straight waveguide, turns smaller as in a curvature waveguide. According to Snell's law, as the incident angle becomes small, the reflected beam becomes small and the accompanying energy loss refracts away from the waveguide.

The curvature loss of a waveguide is usually evaluated by the curvature radius. According to the ray optics, every single period of distance may need a bigger angle for turning while in smaller curvature radius and bigger curvature; same, a smaller incident angle comes with a lower refractive index to result in greater percentage of power loss. Therefore, to decrease the curvature loss of the waveguide, it is better to enlarge the curvature radius, in other words, the curvature shall be smaller so as to that having a smooth curvature.

Figure 11:
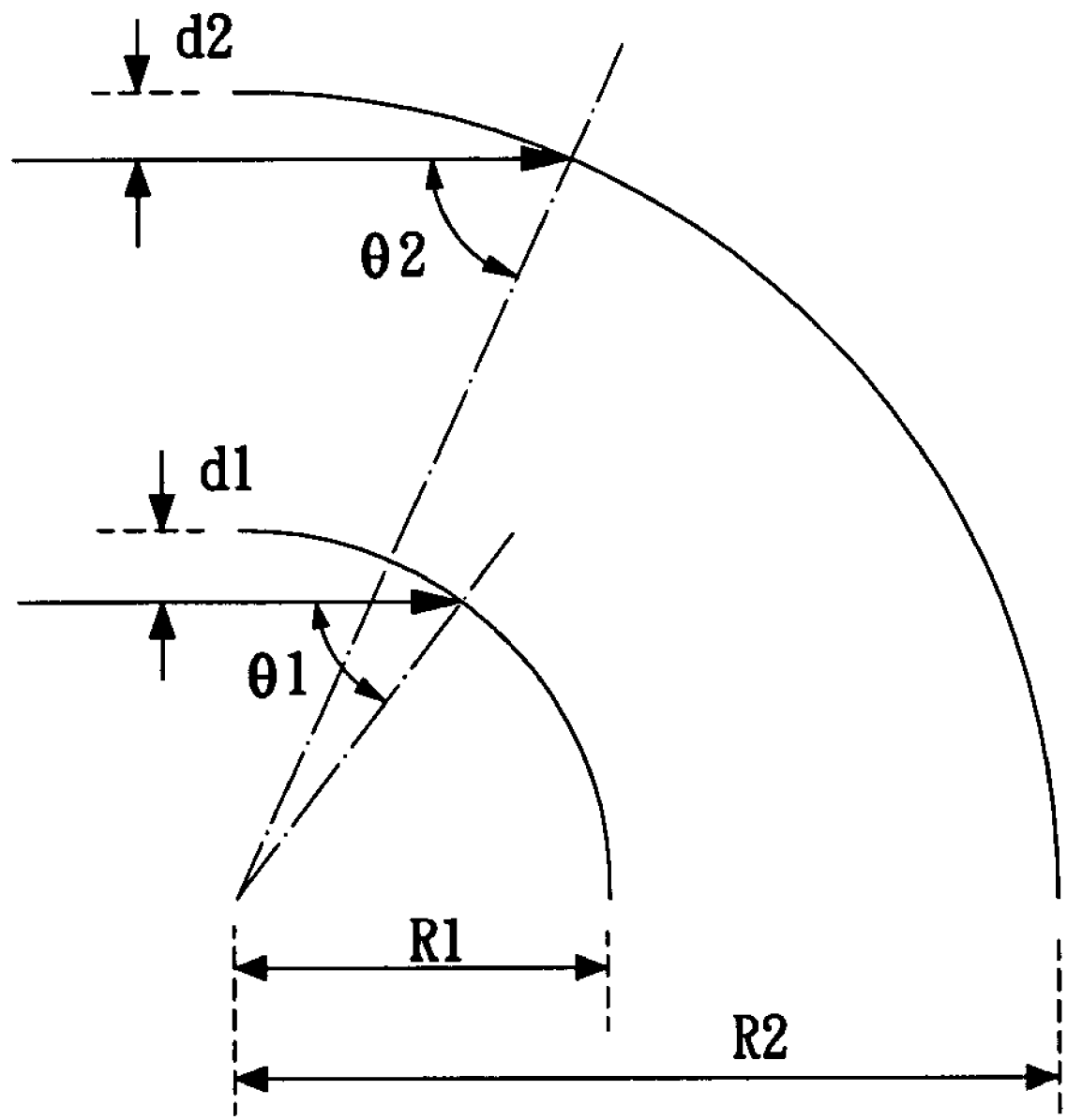
FIG. 11 is a schematic showing curvature radius versus loss.

Please refer to FIG. 11, which is a schematic showing curvature radius versus loss; The figure shows R1<R2. As d1=d2, θ2>θ1 and it clearly represents that the larger the curvature radius becomes, the larger the incident angle is, and more reflection yet less loss.

In order to simplify the design of system interface, one would prefer to align the input and output to the same side of device, and a width of a chip to the extent of enclosing coupling lenses for both the input and output. For example, in case of using a semicircle curvature with a radius of 1 cm, it would require a minimum of 2 cm width of the chip to minimize the curvature energy loses. However, for a sinusoidal curvature, one can achieve a width of 2 cm and a length less than 1 cm where the area occupied will be depend on the minimum curvature radius. Suppose a waveguide has equations for a sinusoidal curvature as follows:

$$x = A\sin\left(\frac{2\pi}{B}y\right) \text{ or}$$
$$y = A\sin\left(\frac{2\pi}{B}x\right) \text{ or}$$
$$x = A\cos\left(\frac{2\pi}{B}y\right) \text{ or}$$
$$y = A\cos\left(\frac{2\pi}{B}x\right),$$

The values of amplitude (A) and wavelength (B) are depending on the refractive index difference between waveguide core layer and the cladding layer, Δn, which also effects the curvature loss, and the relations of the both are based on experiments. As Δn is known, the minimum curvature radius will be known from databases. By knowing the minimum curvature radius, the required amplitude (A) and wavelength (B) for the minimum area purpose with a loss within an acceptable range can thus be achieved.

[Waveguide Coupling to SPR Sensor]

As aforesaid, to achieve coupling shall be with the condition of $k_x=k_{sp}$. In a waveguide, SPR and dispersion relationship is known by $$k_{sp} = \frac{\omega}{c}\sqrt{\frac{\varepsilon_m(\omega)\varepsilon_s(\omega)}{\varepsilon_m(\omega)+\varepsilon_s(\omega)}}$$

The frequency achieving SPR can then be obtained by graphically identifying the intersection of two curves, $k_x$ and $k_{sp}$, the wavelength may then be determined by the frequency. Theoretically, the frequency on the spectrum drops dramatically, since its energy becomes SPW to loss.

[SPR Sensors Using Waveguides]

I. Detection by Light Intensity Variation

Figure 9:
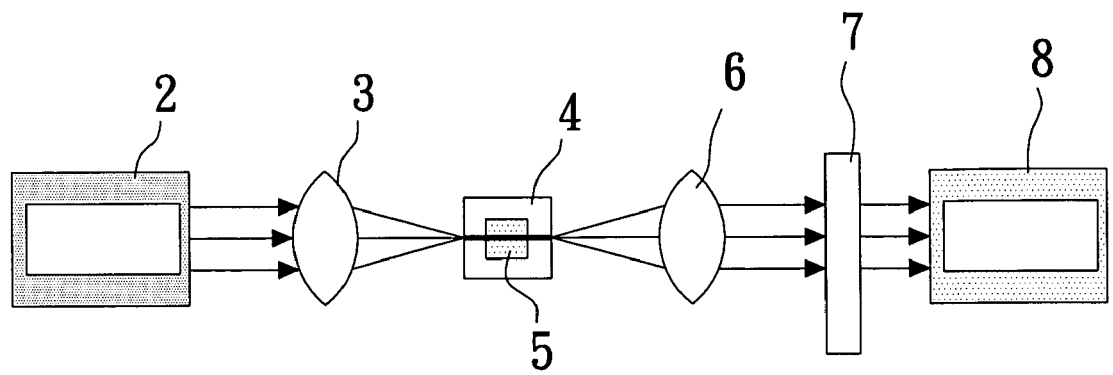
FIG. 9 is a schematic of detecting the intensity variation of light.

FIG. 9 shows that the architecture for the detection by light intensity variation is taking laser as the light source 2, where the light beam propagates through the first optical device 3, impinges into the waveguide 4, passes through the second optical device 6 and the third optical device 7, and finally arrives in the optical spectrometer 8. Due to the single-wavelength laser beam by the light source 2 and limited modes of propagation by the waveguide 4, the incident wave vector can be obtained through the waveguide dispersion. The surface plasmon wave vector is determined by the tested object 5 and the dielectric constant of the metal film; therefore, as the light wave vector matches the surface plasmon wave vector, the intensity of output light decays, which relates to the dielectric constant value of the tested object. This is the principle employed to detect the object-under-test on the metal film.

Figure 12:
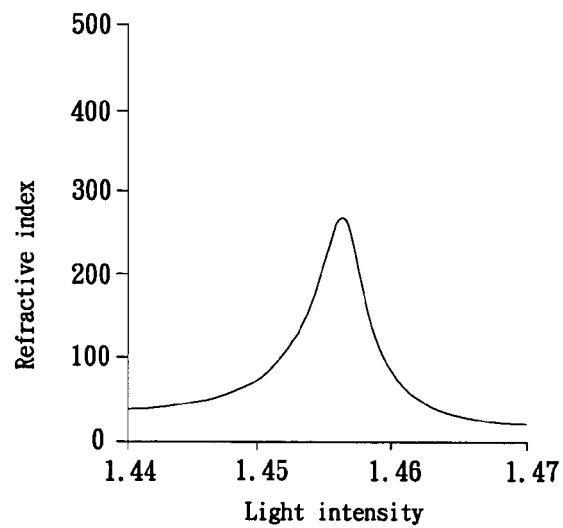
FIG. 12 is a schematic showing light intensity versus refractive index of an tested object.

FIG. 12 is a schematic showing light intensity variation versus refractive index of an tested object;

II. Detection by Resonant Wavelength

Figure 10:
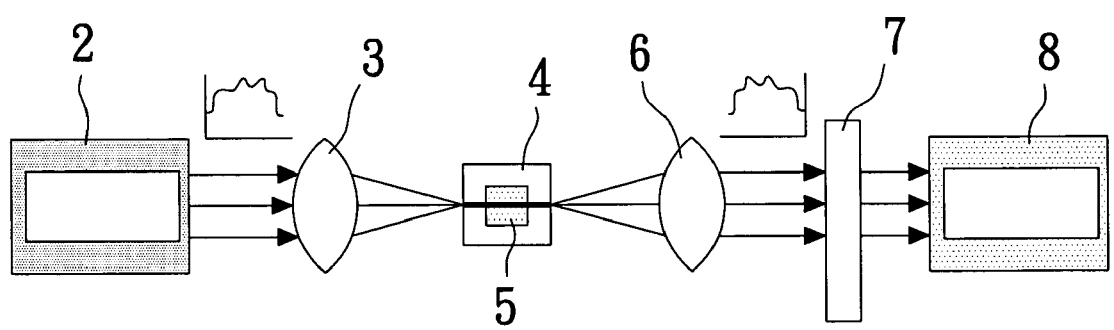
FIG. 10 is a schematic of detecting the wavelength variation of light.

FIG. 10 is the architecture of detecting the wavelength variation of light. The detection configuration takes white light as the light source 2, where the light beam propagates through the first optical device 3, impinges into the waveguide 4, passes through the second optical device 6 and the third optical device 7, and finally arrives in the optical spectrometer 8. As the white light impinges into the waveguide 4, the spectrum of the light source 2 is continuous, which means the light from light source 2 includes all types of frequencies, and in case of the waveguide propagating light with the same mode, the wave vectors of each different wavelength can be acquired from the waveguide dispersion, because white light is broken apart into the colors of the visible light spectrum. The surface plasmon wave vector is determined by the tested object 5 and the dielectric constant of the metal film; therefore, as the light wave vector of a certain wavelength matches the surface plasmon wave vector, the intensity of output light of this wavelength decays, which relates to the dielectric constant value of the tested object. In other words, a different tested object will result in decaying for a different wavelength; moreover, by measuring a wavelength in a drastic decay, it is then available for detecting the dielectric constant of that tested object on the metal film.

Figure 13:
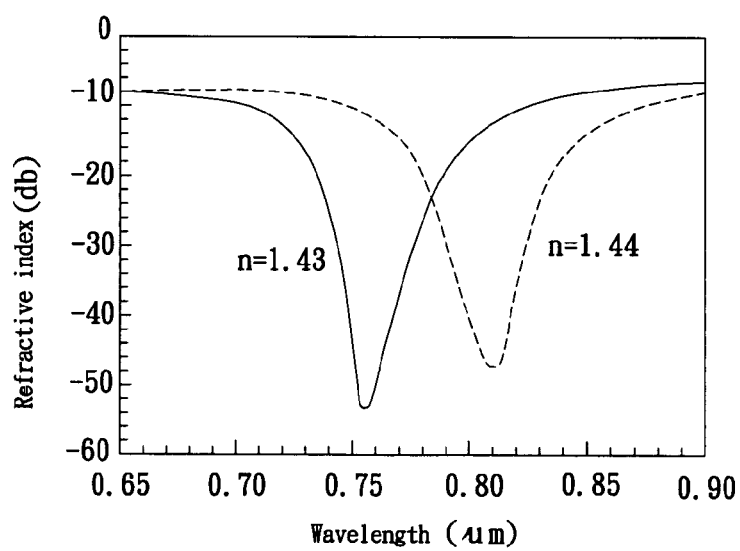
FIG. 13 shows refractive index versus SPR wavelength.

Please refer to FIG. 13 for the relationship between refractive index and SPR wavelength.

The First Embodiment

FIG. 1 is a schematic view of a miniature SPR waveguide device with dual sinusoidal curvatures for compensation of the present invention. An waveguide structure 20 on a substrate 10 has dual sinusoidal curvatures 22 for compensation which combine to form a Y-shaped structure 24.

Figure 2:
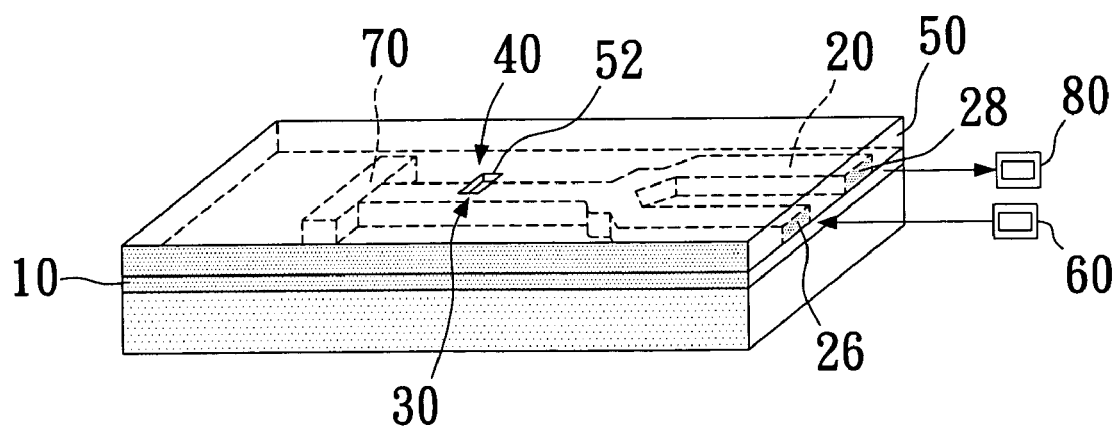
FIG. 2 is a sectional side view of the miniature SPR waveguide device with dual sinusoidal curvatures for compensation of the present invention.

FIG. 2 is a sectional side view of a miniature SPR waveguide device with dual sinusoidal curvatures for compensation of the present invention. The miniature SPR waveguide device 100 with dual sinusoidal curvatures for compensation comprises: a substrate 10; an waveguide structure 20, having sinusoidal curvatures for compensation and resting on top of the substrate 10; a sensing film layer 30, standing at a specific area on top of the waveguide structure 20 where the specific area is a sensing area 40; and a cover layer 50, covering the whole device and having a hole 52 around the sensing area 40; wherein the waveguide structure 20 possesses a light beam input port 26 and a light beam output port 28; a lens device 70 standing on one side of the Y-shaped structure 24.

Based on the above structure, the light beam generated by the light source generator 60 impinges into the input port 26 of the waveguide structure 20, propagates along the path with dual sinusoidal curvatures 22 for compensation, passes across the sensing area 40 and through the lens device 70, and finally emits from the output port 28 of the waveguide structure 20 to the spectrometer 80.

The Second Embodiment

Figure 3:
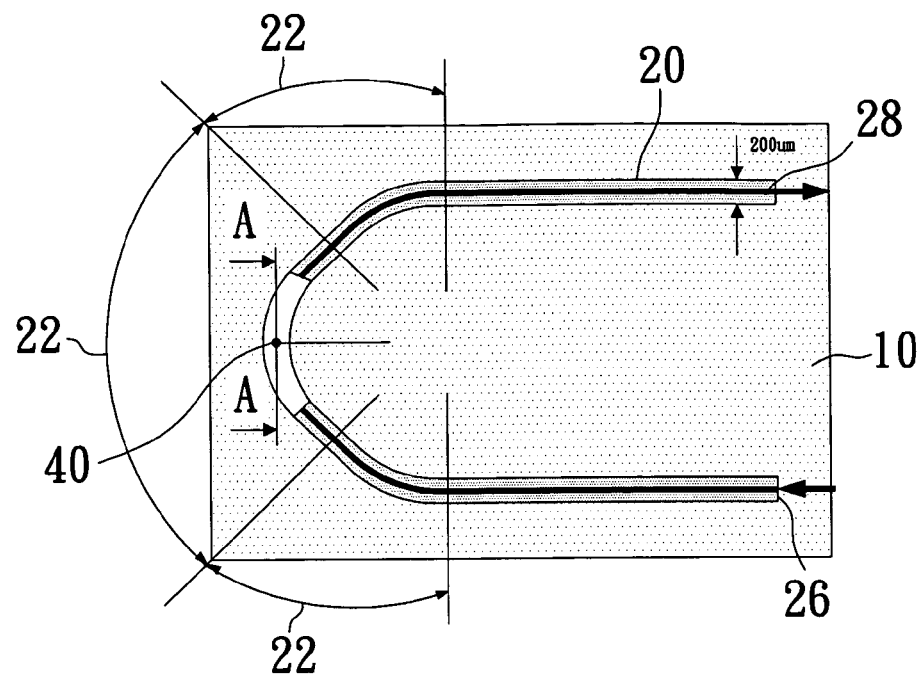
FIG. 3 is a schematic view of another embodiment of the present invention.

FIG. 3 is a schematic view of another embodiment of the present invention. An waveguide structure 20 on top of a substrate 10 has a shape with triple sinusoidal curvatures 22 for compensation.

Figure 4:
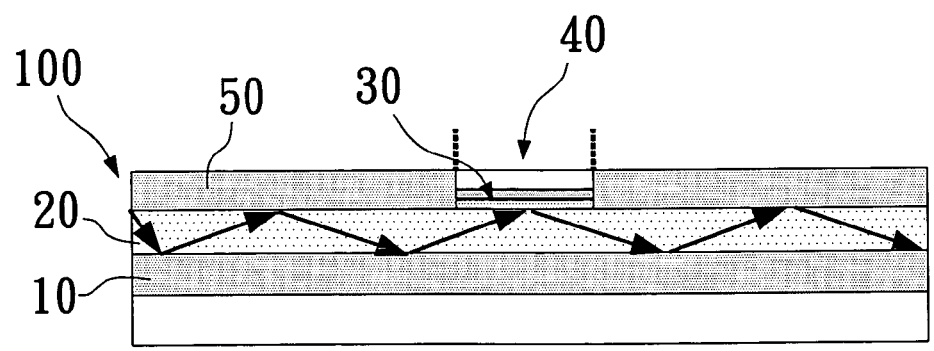
FIG. 4 is a sectional side view showing the portion of A–A' of FIG. 3.

FIG. 4 is a sectional side view showing the portion of A–A' of FIG. 3. A miniature SPR waveguide device 100 with dual sinusoidal curvatures for compensation comprises: a substrate 10; an waveguide structure 20, having dual sinusoidal curvatures for compensation and resting on top of the substrate 10; a sensing film layer 30, standing at a specific area on top of the waveguide structure 20 where the specific area is a sensing area 40; and a cover layer 50, covering the whole device and having a hole 52 around the sensing area 40; wherein the waveguide structure 20 possesses a light beam input port 26 and a light beam output port 28.

In this embodiment, the sensing film 30 is made by a gold (Au) film and a silver (Ag) film, and the Au film is deposited on top of the Ag film. Ag has higher activity (easier oxidize by the surroundings) so that it will be Au on top of Ag and the order of layers is Au/Ag/glass. The advantages for plating both Au and Ag are: (1) SPR curve (on plot of loss versus resonant wavelength) is about the same with that of Au only (but shift more with respect to that of Ag only), (2) signal to noise ratio (SNR) is higher than that of Au only (between Au only and Ag only), (3) the top layer of Au film can protect the bottom Ag film from direct exposure for oxidization. Therefore, a multi-layer design may improve surface characteristics of the metal film and also may raise the sensitivity of the detections.

In the above two embodiments, the substrate 10 is made out of the materials: silicon, silicon dioxide or polymers; the waveguide structure 20 is composed of photoresists, silicon dioxide, doped silicon dioxides, or polymers, where the materials fit guide wavelengths of 400 nm~1100 nm are the superior; the sensing film is made out of metals; the cladding layer is composed of photoresists, silicon dioxide, doped silicon dioxides, dielectric materials or polymers.

Figure 5:
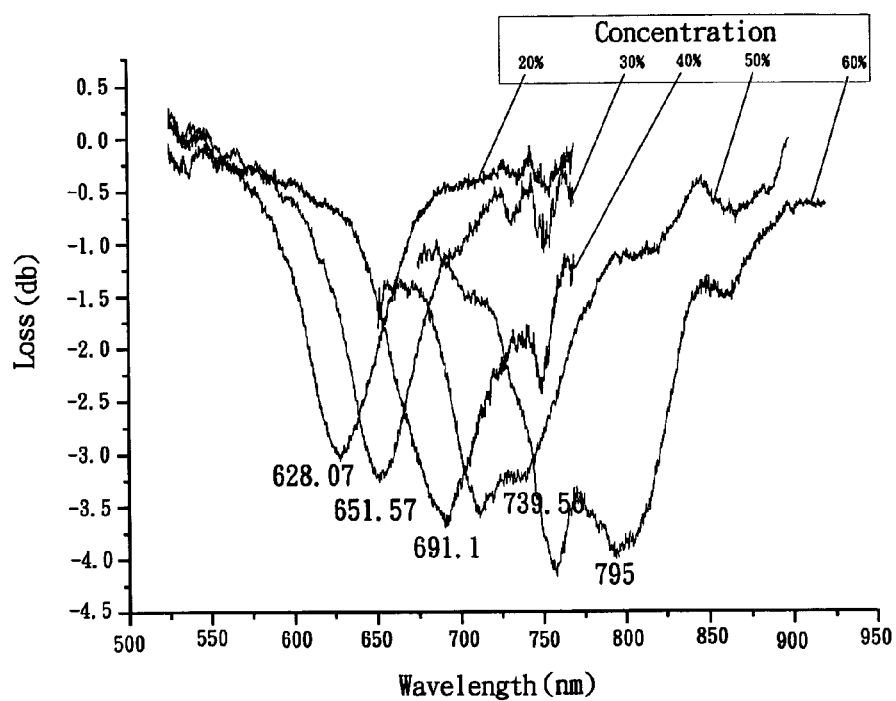
FIG. 5 shows SPR wavelengths of glycerin regard to different concentrations.
Figure 6:
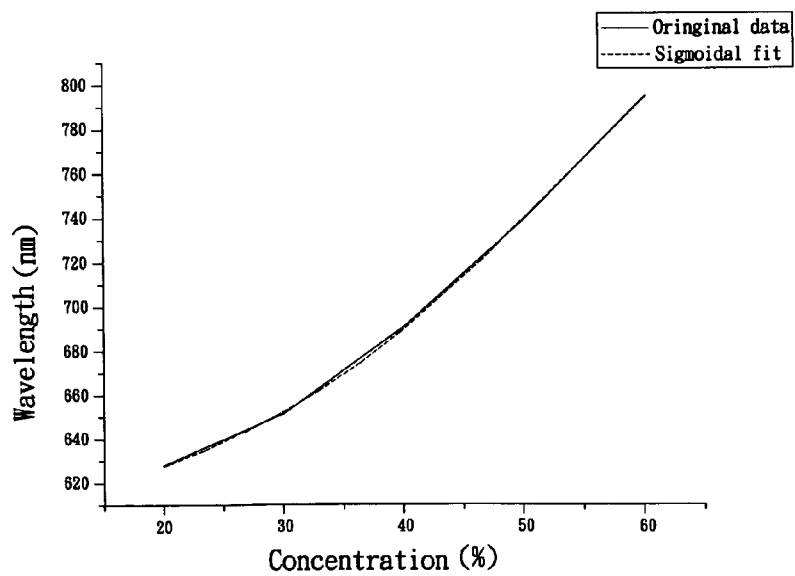
FIG. 6 shows concentration versus SPR wavelength.
Figure 7:
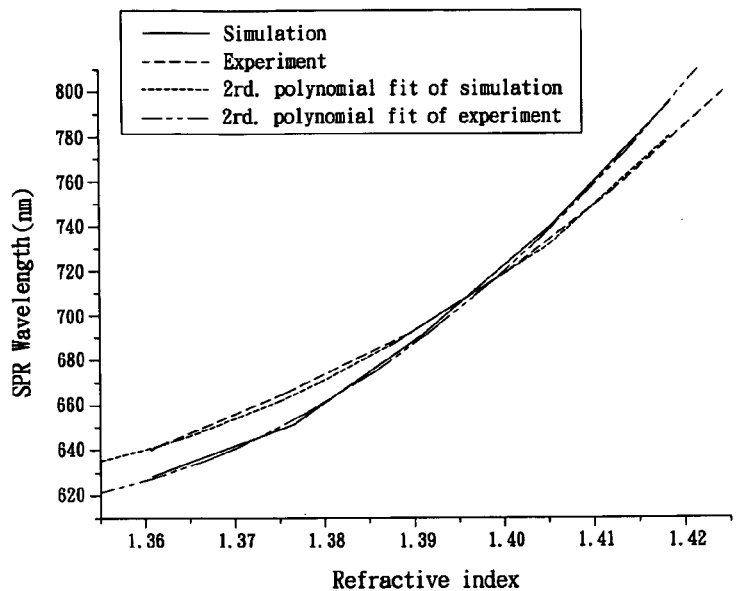
FIG. 7 shows refractive index versus SPR wavelength.
Figure 8:
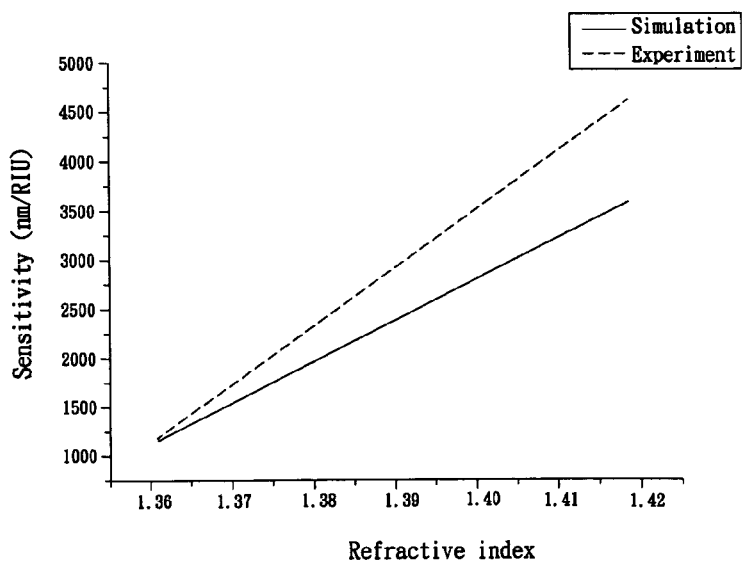
FIG. 8 shows refractive index versus sensitivity.

FIG. 5 to FIG. 8 are the experimental data plots of the detections exploiting the present invention. FIG. 5 represents SPR for various wavelengths by the different concentrations of glycerin. FIG. 6 shows concentrations versus wavelengths. FIG. 7 shows refractive indexes versus wavelengths, where dotted lines represent theoretical simulations while solid lines represent experimental results, and the result evidence is that the resonant wavelengths by the experiments are higher than those by the theoretical simulations. FIG. 8 shows refractive indices versus sensitivities, where dotted lines for theoretical simulations while solid lines for experimental results, and the sensitivities by the experiments are higher than those by the theoretical simulations.

As a consequence, the present invention exploits aspects of SPR to research and design a waveguide type of SPW sensing device, which features a high sensitivity, high throughput screening and low cost in the condition without the use of labeled molecules. To meet the trend of miniaturizing and precise in the design of optical mechanism, a light source in the frequency range of visible light spectrum to near infrared is selected. By utilizing curvature compensation of preferred design, energy loss within an acceptable range under the limitation of the minimum curvature radius, coupled with a shrink in chip size and a plated metal film with the specific wavelength for SPR, and a magnifying ratio of sensing area to length of the light coupler to diminish sample amount, the goal of a high sensitivity while realizing novelty is achieved. Based on the above improvements, the present invention is extremely fit for the applications of the miniature biosensors.

While the present invention has been shown and described with reference to a preferred embodiment thereof, and in terms of the illustrative drawings, it would not be considered as limited thereby. Various possible modifications, omissions, and alterations could be conceived of by one skilled in the art to the form and the content of any particular embodiment, without departing from the scope of the present invention.

What is claimed is:

1. A miniature surface plasmon resonance device with sinusoidal curvature compensation, comprising:
   a substrate;
   an waveguide structure, said structure having sinusoidal curvature compensation, resting on top of said substrate, and having a light input port and a light output port;
   a sensing film layer, standing at a specific area on top of said waveguide structure, where the specific area is a sensing area; and
   a cover layer, covering said waveguide device and having a hole at said sensing area;
   based on said waveguide structure having sinusoidal curvature for compensation, a light beam guided into said light input port of said waveguide structure, propagating along a path with said sinusoidal curvature for compensation, passing across said sensing area, and emitting from said light output port of waveguide structure.

2. The miniature surface plasmon resonance device with sinusoidal curvature compensation as claimed in claim 1, further comprising a light source generator, capable of providing light signal impinging into said light input port.

3. The miniature surface plasmon resonance device with sinusoidal curvature compensation as claimed in claim 1, further comprising a spectrometer, capable of receiving light signal emitting from said light output port.

4. The miniature surface plasmon resonance device with sinusoidal curvature compensation as claimed in claim 1, wherein said substrate is made by some of the following: silicon, silicon dioxide and polymers.

5. The miniature surface plasmon resonance device with sinusoidal curvature compensation as claimed in claim 1, wherein said waveguide structure is composed by some of the following: photoresist, silicon dioxide, doped silicon and polymers.

6. The miniature surface plasmon resonance device with sinusoidal curvature compensation as claimed in claim 1, wherein said waveguide structure is composed of materials fit for guide wavelengths of 400 nm ~1100 nm.

7. The miniature surface plasmon resonance device with sinusoidal curvature compensation as claimed in claim 1, wherein said waveguide structure has dual sinusoidal curvatures for compensation that combine to form a Y-shaped structure.

8. The miniature surface plasmon resonance device with sinusoidal curvature compensation as claimed in claim 7, further comprising a lens device, said device standing at one end of said Y-shaped structure.

9. The miniature surface plasmon resonance device with sinusoidal curvature compensation as claimed in claim 8, wherein said lens device is made out of metals.

10. The miniature surface plasmon resonance device with sinusoidal curvature compensation as claimed in claim 1, wherein said waveguide structure has triple sinusoidal curvatures for compensation to form a structure.

11. The miniature surface plasmon resonance device with sinusoidal curvature compensation as claimed in claim 1, wherein said sensing film layer is made out of metals.

12. The miniature surface plasmon resonance device with sinusoidal curvature compensation as claimed in claim 1, wherein said sensing film layer is a gold (Au) film.

13. The miniature surface plasmon resonance device with sinusoidal curvature compensation as claimed in claim 1, wherein said sensing film layer is a combination of a gold (Au) film and a silver (Ag) film.

14. The miniature surface plasmon resonance device with sinusoidal curvature compensation as claimed in claim 13, wherein said sensing film layer has said gold (Au) film on top of said silver (Ag) film.

15. The miniature surface plasmon resonance device with sinusoidal curvature compensation as claimed in claim 1, wherein said cover layer is composed by some of the following: photoresist, silicon dioxide, doped silicon and said polymers.

* * * * *